United States Patent [19]
DiGiacomo et al.

[11] 4,235,990
[45] Nov. 25, 1980

[54] LAYERED CARBOXY END TERMINATED ORGANOPHOSPHORUS INORGANIC POLYMERS

[75] Inventors: Peter M. DiGiacomo, Mission Viejo; Martin B. Dines, Santa Ana, both of Calif.

[73] Assignee: Occidental Research Corporation, Irvine, Calif.

[21] Appl. No.: 952,228

[22] Filed: Oct. 17, 1978

[51] Int. Cl.$^2$ ............................................. C08L 85/02
[52] U.S. Cl. ................................ 528/287; 260/429 R; 260/429.1; 260/429.2; 260/429.3; 260/429.5; 260/435 R; 528/395; 528/398
[58] Field of Search ............ 260/429.3, 429 R, 435 R, 260/429.5, 429.1, 429.2; 528/395, 398, 287

[56] References Cited

U.S. PATENT DOCUMENTS

| | | | |
|---|---|---|---|
| 3,052,653 | 9/1962 | Iannicelli | 260/429 R X |
| 3,310,575 | 3/1967 | Spivack | 260/429 R |
| 3,444,103 | 5/1969 | Maguire | 260/429 R X |
| 4,063,923 | 12/1977 | Han | 260/429 R X |

OTHER PUBLICATIONS

Yamanaka et al., Clays & Clay Minerals 23, pp. 477–478 (1975).
Michel et al., L. Naturforschung 20 B, pp. 1307–1308 (1965).
Yamanaka, Inorganic Chem. 15 (11) 2811, (1976).
Alberti et al., J. of Inorg. and Nuclear Chem. 40 (6), pp. 1113–1117 (1978).
Chemical Abstracts, 77, 157135k (1972).
Chemical Abstracts, 80, 41506q (1974).

*Primary Examiner*—Helen M. S. Sneed
*Attorney, Agent, or Firm*—Christie, Parker & Hale

[57] ABSTRACT

Carboxy phosphorus acid compounds react by a metathesis reaction in a liquid media with tetravalent metal ions to yield layered crystalline inorganic polymers having the empirical formula $M(O_3PR_nCOOH)_2$ where M is a tetravalent metal and R is an organic group covalently bonded to phosphorous and the terminal carboxy group and n is 0 or 1.

11 Claims, 12 Drawing Figures

SEMI CRYSTALLINE
$Zr(O_3PCH_2CH_2CO_2H)_2$

HIGHLY CRYSTALLINE
$Zr(O_3PCH_2CH_2CO_2H)_2$

← 2ν

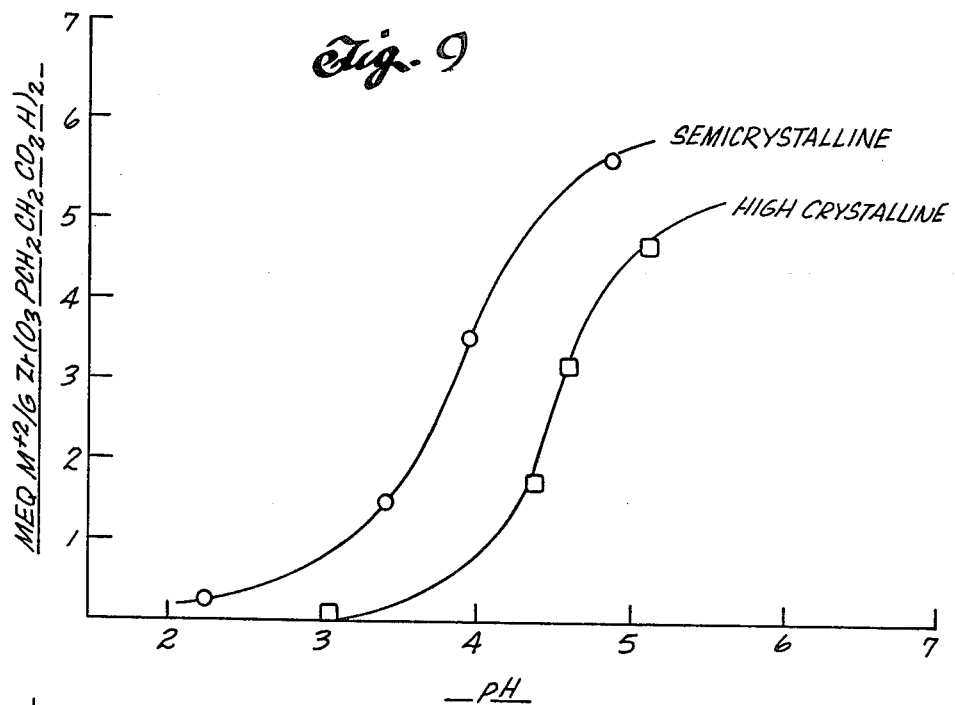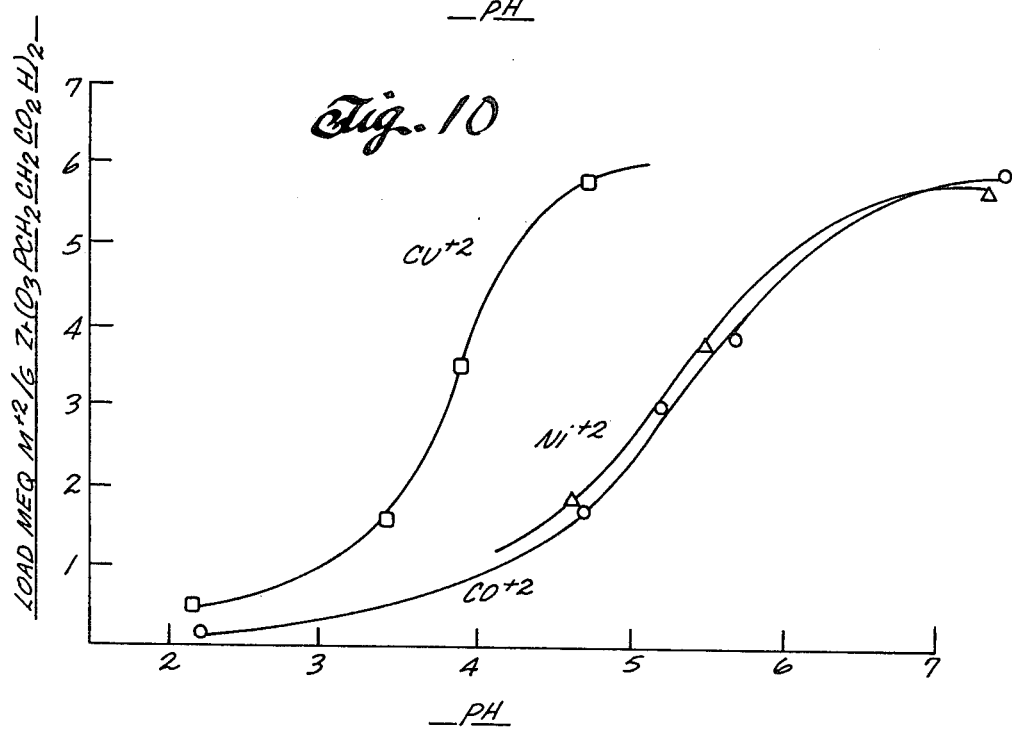

LAYERED CARBOXY END TERMINATED ORGANOPHOSPHORUS INORGANIC POLYMERS

CROSS REFERENCE TO RELATED APPLICATIONS

This application is related to our application Ser. No. 945,971 filed on Sept. 26, 1978 and titled "Process for Preparing Layered Organophosphorous Inorganic Polymers," the entire disclosure of which is hereby incorporated herein by this reference.

BACKGROUND OF THE INVENTION

The present invention is directed to solid inorganic polymers having carboxy groups anchored to the surfaces of the polymers. The polymers formed can be layered crystals which display intercalation activity, or they can be partially or totally amorphous.

The interface surfaces of solids are responsive regions of chemical and physical action. Many practical chemical and physical phenomena such as absorption, corrosion, inhibition, heterogeneous catalysis, lubrication, ion exchange activity, adhesion and wetting and electrochemical activity occur on or as a consequence of the presence of a definable solid surface. Solid agents are preferred in most processes over solution or homogeneously dispersed reactive alternatives primarily because they greatly signify efficient separation of products from reactants. However, solids invariably suffer from deficiencies in activity and selectivity in the conversions they effect, due to inherent heterogeneity in the active sites which arises from the nature of their surface structure. Furthermore, much of the active sites are usually buried within the surface, and as a result of these two factors, elevated temperature and low conversions are typically required to make a process effective. Exceptions in which homogeneous agents have been used include the Monsanto process for the production of acetic acid from methanol and carbon monoxide employing rhodium, the production of linear alcohols from olefins and syngas, ethylene oxidation by the Wacker process, catalysis of olefins to form polymers, and other polymerization systems.

In an effort to achieve the best features of both homogeneous and heterogeneous processes, efforts have been made to chemically "anchor" known effective solution agents such as phosphines, nitriles, cyclopentadiene and the like, onto certain solids. Porous inorganic surfaces and insoluble organic polymers have been employed. Silica has been the inorganic of choice, the bonded ligand being attached by reaction with the —OH groups projecting from the surface. The organic polymer most used has been polystyrene, with an appropriate metal-coordinating function bonded via the phenyl rings. Results have been generally encouraging. However, there have been pervasive problems deriving from the non-uniform situation of sites which has manifested itself in loss of expected selectivity, activity and even in attrition.

Many inorganic solids crystallize with a layered structure and present sites for anchoring active groups. In this form, sheets or slabs with a thickness of from one to more than seven atomic diameters lie upon one another. With reference to FIG. 1, strong ionic or covalent bonds characterize the intrasheet structure, while relatively weak van der Waals or hydrogen bonding occurs between the interlamellar basal surfaces, in the direction perpendicular to their planes. Some of the better known examples are prototypal graphite, most clay minerals, and many metal halides and sulfides. A useful characteristic of such materials is the tendency to incorporate "guest" species in between the lamella.

In this process, designated "intercalation", the incoming guest molecules, as illustrated in FIG. 2, cleave the layers apart and occupy the region between them. The layers are left virtually intact, since the crystals simply swell in one dimension, i.e., perpendicular to the layers. If the tendency to intercalate is great, then the host layered crystal can be thought of as possessing an internal "super surface" in addition to its apparent surface. In fact, the potential surface is greater than the actual surface by a factor of the number of lamella composing crystal. This value is typically on the order of $10^2$–$10^4$. Although edge surface is practically insignificant compared to basal surface, it is critical to the rate of intercalation, since the inclusion process always occurs via the edges. This is because bonding within the sheets is strong, and therefore, penetration of the sheets is an unlikely route into the crystal.

Previous studies of the intercalative behavior of layered compounds have mainly been conducted by solid-state chemists interested in the bulk effects on the layered host materials. Graphite has, for example, been extensively studied from an electronic point of view. In general, the function of the host is essentially passive. That is, on intercalation the host serves as the matrix or surface with which the incoming guest molecules interact, but throughout the process and on deintercalation the guests undergo only minor perturbation.

In order for a more active process to occur during intercalation, such as selective fixation or catalytic conversion, specific groups must be present which effect such activity. There might also be some preferable geometric environment about each site, as well as some optimal site-site spacing. These considerations have not been extensively applied to intercalation chemistry simply because such kinds of active groups required are not found on layered surfaces.

An approach in which catalytically active agents have been intercalated into graphite or clays for subsequent conversions has been described in "Advanced Materials in Catalysis", Boersma, Academic Press, N.Y. (1977), Burton et al, editors, and "Catalysis in Organic Chemistry", Pinnavia, Academic Press, N.Y. (1977), G. V. Smith, editor, each incorporated herein by reference. In neither case could it be shown that any activity was occurring within the bulk of the solid. Rather, it is believed that edge sites are responsible for the reactivity observed. In none of the cases was the active site covalently anchored, or fixed upon the lamella of the host. Instead, the normal ionic or van der Waals forces of intercalated guests were operating.

One of the few layered compounds which have available sites is zirconium phosphate $Zr(O_3POH)_2$. It exists in both amorphous and crystalline forms which are known to be layered. In the layered structure, the site-site placement on the internal surfaces is about 5.3 Å, which leads to an estimated 25 Å$^2$ area per site. This area can accomodate most of the functional groups desired to be attached to each site. The accepted structure, symbolized projection of a portion of a layer of this inorganic polymer and a representation of an edge view of two layers, are shown respectively in FIGS. 3, 4 and 5.

Besides the advantageous structural features of zirconium phosphate, the material is chemically and thermally stable, and non-toxic.

Quite a bit of work has been conducted on the zirconium phosphate, mainly because it has been found to be a promising inorganic cation exchanger for alkali, ammonium and actinide ions, Alberti, "Accounts of Chemistry Res." 11, 163, 1978, incorporated herein by reference. In addition, some limited work has been described on the reversible intercalation behavior of layered zirconium phosphate toward alcohols, acetone, dimethylformamide and amines, Yamaka and Koizuma, "Clay and Clay Minerals" 23, 477 (1975) and Michel and Weiss, "Z. Natur," 20, 1307 (1965) both incorporated herein by reference. A. Yamaka described the reaction of this solid with ethylene oxide, which does not simply incorporate between the layers as do the other organics, but rather was found to irreversibly react with the acidic hydroxyls to form a covalent bonded product, Yamaka, "Inorg. Chem." 15, 2811, (1976). This product is composed of a bilayer of anchored ethanolic groups aimed into interlayers. The initial layer-layer repeat distance is expanded from about 7.5 Å to 15 Å, consistent with the double layer of organics present. The overall consequence of this reaction is to convert inorganic acid hydroxyls to bound organic alkanol groups. This conversion, while of interest, has limited if any improvement over the hydroxyls already available on zirconium phosphate.

Attempts have been made to add other moieties to zirconium phosphate. Results have only been successful with respect to exposed surfaces. No practical route was found to add them to the internal surfaces and such a route is necessary if the full super surface of the crystals are to be made utile.

Summary of the Invention

According to the present invention there is provided inorganic polymers having carboxy groups pendant to phosphorus atoms wherein the phosphorus atoms are, in turn, linked by oxygen to tetravalent metal atoms. The pendant carboxy groups are coupled to phosphorus directly or through an organic group.

Compounds provided in accordance with the invention are inorganic polymers providing pendant carboxy groups and which include units of the formula:

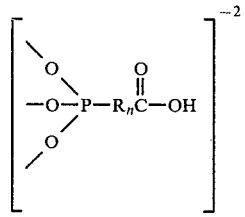

wherein n is 0 or 1, R is an organo group and in which the phosphorus is structurally linked through each of the available oxygens to a tetravalent metal selected from the group consisting of zirconium, cerium, thorium, uranium, hafnium, lead, titanium, and mixtures thereof and wherein the molar ratio of phosphorus to tetravalent metal in said inorganic polymer is about 2 to 1.

Carboxy homopolymers which are inorganic phosphonate polymers have the empirical formula:

wherein n and R are as defined above with R, if present, linked to phosphorus through carbon and M is a tetravalent metal. When n is 1, typically R contains from 1 to about 17 carbon atoms, preferably from 1 to about 6 carbon atoms. When n is 0, the —COOH group is directly bonded to phosphorus.

The compounds of the invention are formed by a liquid media reaction in which at least one carboxy phosphorus acid compound of the formula:

wherein n and R are as defined above is reacted with at least one tetravalent metal ion selected from the group consisting of zirconium, cerium, thorium, uranium, lead titanium and mixtures thereof. The molar ratio of phosphorus to the tetravalent metal in the product is 2 to 1. Reaction, however, preferably occurs in the presence of an excess of phosphorus containing acid reactants to consume all of the metal ions and the metal ion is provided as a compound soluble in the liquid media.

Other organophosphorus acid compounds may be present for reaction to form part of the inorganic polymer which is the product of the reaction. These organophosphorus acid compounds need not contain carboxy functions. They may contain substituents which have functional groups that interact with the carboxy groups in the product. Donor functional groups such as nitrile, ether, ester, amide, oxo, hydroxy, sulfide, hydrosulfide and the like influence the ion exchange selectivity and the acidity of nearby carboxy groups. These substitutents may also contain ionic groups thereby rendering the products ampholytic salt exchangers. Phosphoric and/or phosphorous acid can also be present as reactive dilutants.

The products formed are layered crystalline to semicrystalline to amorphous in nature. The pendant carboxy groups serve as ion exchange resins and as intermediates for the addition or substitution of other functional groups.

Multicomponent polymers, containing other organic groups interspersed with the carboxyl group, can be prepared. In addition, a mixture of two or more carboxylic acids can be used in the preparation, e.g., one acyclic and one cyclic acid.

THE DRAWINGS

Figure 1:
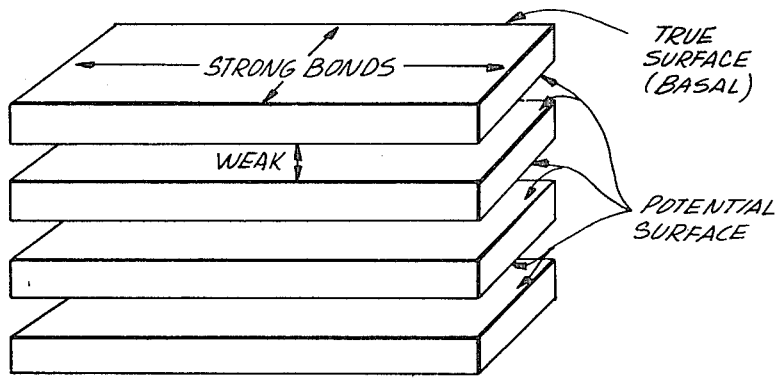
FIG. 1 illustrates a layered microcrystal. Each lamellar slab is formed of strong covalent bonds and has a thickness of about 10 atoms.
Figure 2:
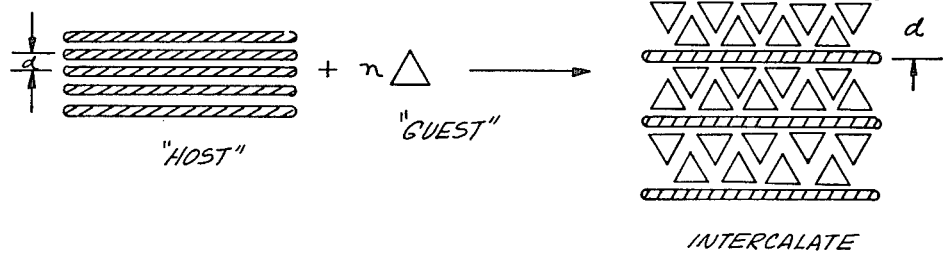
FIG. 2 illustrates intercalation where the interlayer distance is shown as "d".
Figure 3:
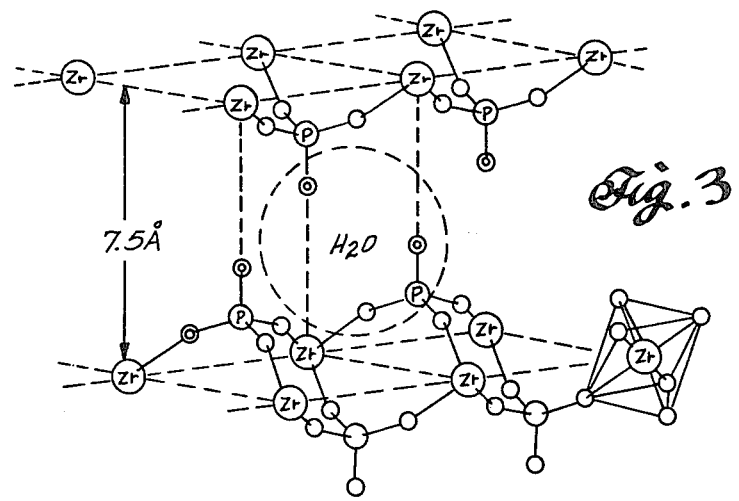

FIG. 3 illustrates the accepted structure for zirconium phosphate and spacing between layers. The dashed lines between zirconium (Zr) atoms is to establish the plane between them. In the drawing P=Phosphorus, O=Oxygen and water of hydration is shown.

Figure 4:
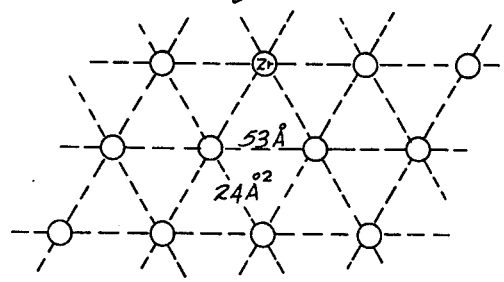

FIG. 4 illustrates a projection of zirconium plane showing accepted spacing between Zr atoms and the available linkage area.

Figure 5:
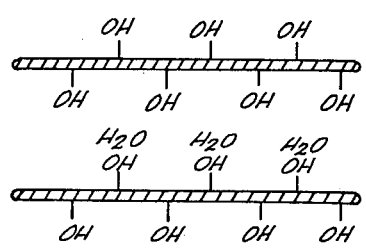

FIG. 5 is a symbolized depiction of spaced zirconium phosphate layers showing covalently bonded hydroxyl groups and water of hydration.

Figure 6:
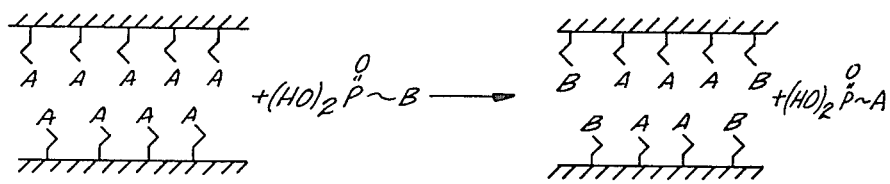
Figure 7:
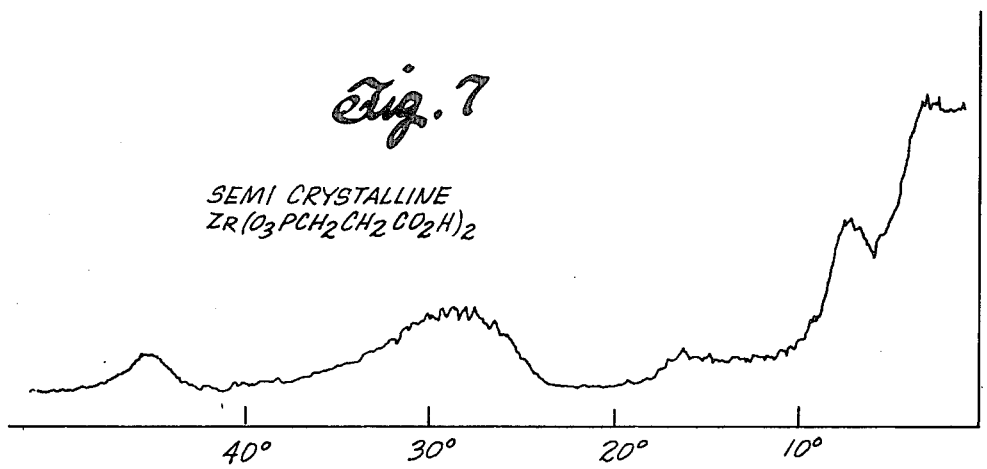

FIG. 6 illustrates an exchange reaction where anchored COOH groups ("A") groups are to be substituted by "B", and ∼ represents the portion of the organo group linking the terminal group "A" or "B" to the crystals or the organophosphorus acid compound reactant. FIG. 7 is an x-ray powder diffraction pattern for semi-crystalline zirconium 2-carboxyethyl phosphonate as prepared in Example 1.

Figure 8:
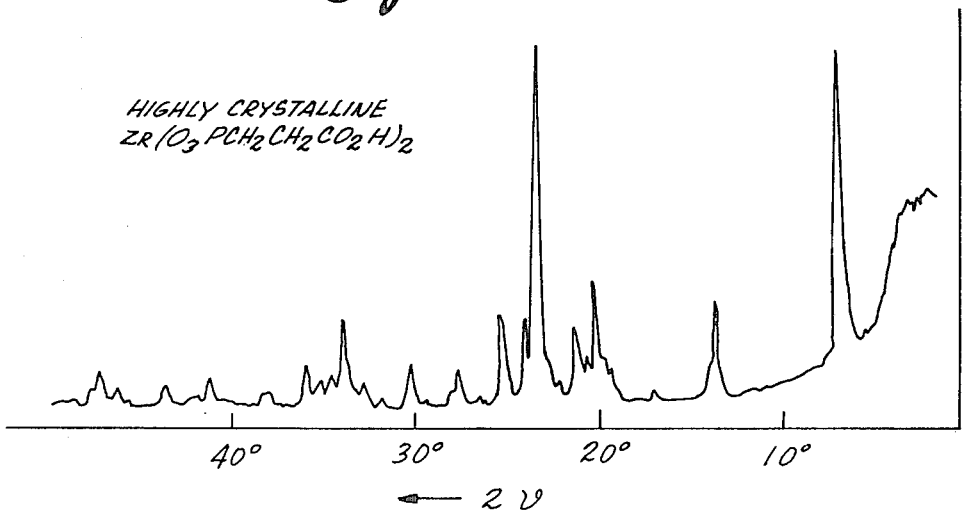

FIG. 8 is an x-ray powder diffraction pattern for highly crystalline zirconium 2-carboxyethyl phosphonate as prepared in Example 2.

FIG. 9 compares the loading of divalent metals on zirconium 2-carboxyethyl phosphonate as a function of pH.

FIG. 10 compares the loading of $Cu^{+2}$ in the semi-crystalline reaction product of Example 1 to the highly crystalline product of Example 2.

Figure 11:
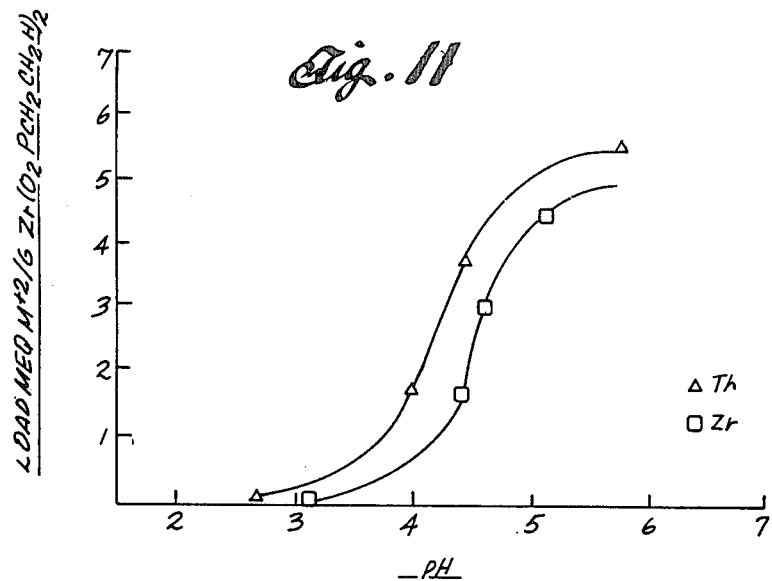

FIG. 11 compares the loading of $Cu^{+2}$ on the reaction product of Example 2 to thorium 2-carboxyethyl phosphonate.

Figure 12:
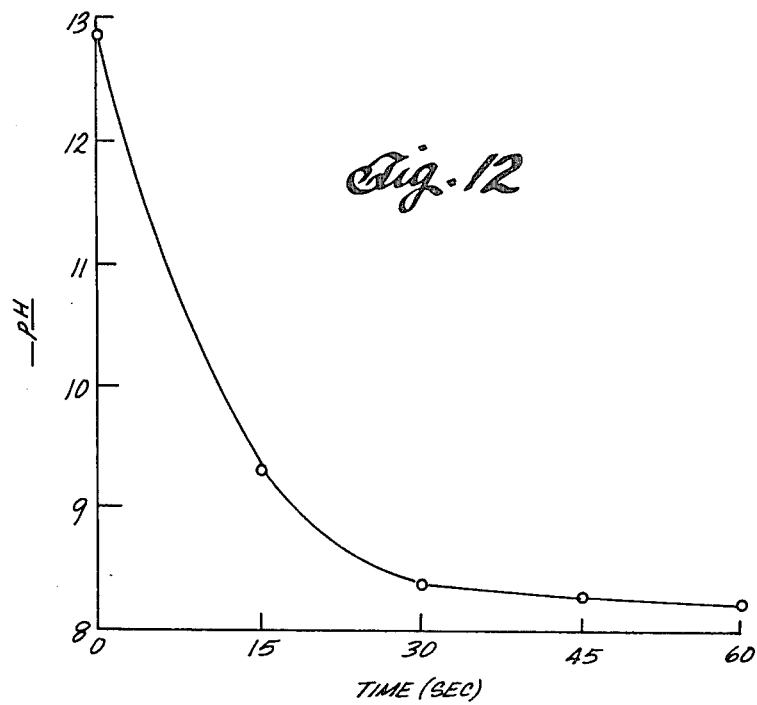

FIG. 12 shows the rate of neutralization of zirconium 2-carboxyethyl phosphonate by sodium hydroxide.

DETAILED DESCRIPTION

According to the present invention there is provided crystalline to amorphous inorganic polymers formed of structural units of the formula:

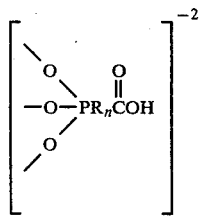

wherein n is 0 or 1, R is an organo group covalently bonding the —COOH group to phosphorus and wherein each phosphorus is linked through oxygen to a tetravelent metal selected from the group consisting of zirconium, cerium, thorium, uranium, lead, titanium, hafnium, and mixtures thereof and wherein the molar ratio of phosphorus to tetravalent metal in said inorganic polymer is about 2 to 1.

Homopolymers are where inorganic phosphonate polymers have the empirical formula:

$$M(O_3PR_nCOOH)_2$$

wherein n is 0 or 1 and R is as defined as above, with R, if present, linked to phosphorus by carbon and M is a tetravalent metal ion selected from the group consisting of zirconium, cerium, thorium, uranium, lead, titanium hafnium and mixtures thereof. Typically, R, if present, contains from 1 to about 17 carbon atoms, preferably from 1 to about 6 carbon atoms. When n is 0, the —COOH group is directly bonded to phosphorus.

The polymers are prepared by a liquid phase metathesis reaction of at least one carboxyphosphorus acid compound having the formula:

$$(HO)_2OPR_nCOOH$$

wherein n is 0 or 1 and R is as defined above with at least one tetravalent metal ion selected from the group consisting of zirconium, thorium, cerium, uranium, hafnium lead, titanium and mixtures thereof to form a solid inorganic polymer precipitate in which phosphorus is linked to the metal by oxygen and the carboxy or carboxy organo group is covalently bonded to the phosphorus atoms. The carboxy group is pendent from the inorganic polymer. Typically, the tetravalent metal ion is provided as a soluble salt MX wherein M is tetravalent metal as defined above and X is the anion(s) of the salt. Typical anions include halides such as $Cl^-$, $HSO_4^{-1}$, $SO_4^{-2}$, $O_2C-CH_3^{-1}$, $NO_3^{-1}$, $O^{-2}$ and the like.

The polymeric reaction products formed have been found to be layered crystalline or semi-crystalline in nature and, as such, provided layered structures similar to zirconium phosphate. The amorphous portion of polymers possessing a large quantity of available pendent groups and is similar to silica gel.

By the term "carboxyphosphorus acid compound," as used herein, there is meant a compound of the formula:

$$(HO)_2OPR_nCOOH$$

wherein n is 0 or 1, R, as COOH, is any organo group which will replace a hydroxyl of phosphoric acid and/or the hydrogen of phosphorous acid and couple to the acid by a covalent bond. Coupling to the acid may be through carbon, oxygen, silicon, sulfur, nitrogen and the like. Coupling through carbon or an oxygen-carbon group is preferred with coupling through carbon particularly preferred.

By the term "organophosphorus acid compound" as used herein, there is meant compounds other than carboxy terminated compounds of the formula:

$$[(HO)_2OP]_xR'$$

wherein x is 1 or 2 and R' is an organo group other than one providing the carboxy. Coupling is preferably through carbon or an oxygen-carbon group and may be used as indicated below as co-reactants or as exchange reactants.

When coupling is through carbon, the carboxyphosphorus acid compound or the organophosphorus acid compound is a carboxy or organo phosphonic acid and the product is a phosphonate. When coupling is through oxygen-carbon, the carboxyphosphorus acid compound or organophosphorus acid compound is a carboxy or organo phosphoric monoester acid and the product a phosphate.

The general reaction for phosphonic acids alone is shown in equation (1) below and for monoesters of phosphoric acid alone by equation (2).

$$M^{+4} + 2(HO)_2PR_nCOOH \rightarrow M(O_3PR_nCOOH)_2 \quad (1)$$

$$M^{+4} + 2(HO)_2P(OR'')_nCOOH \rightarrow M(O_3P(OR'')_nCOOH)_2 \quad (2)$$

wherein R" is the remainder of the organo group "R."

The product contains phosphorus to metal in a molar ratio of about 2 to 1, and the empirical formula for the product would show all groups bound to phosphorus.

In general, the choice of R will affect compound stability, the acidity of the carboxyl group, the hydrophilic-hydrophobic nature of the solid, interlamellar spacing, crystal size, etc.

While nowise limiting, the R groups attachable to phosphorus and the carboxy group may be saturated or unsaturated, substituted and unsubstituted and include, among others, alkyl, alkylene, alkyne, aryl, alkylaryl and the like or can be partially or wholly halogen substituted, e. g., perfluoroalkyl. Typically, the group will contain from about 1 to about 17 carbon atoms, preferably from 1 to about 6 carbon atoms.

While nowise limiting, the R' groups attachable to organophosphorus acid compounds may be saturated and unsaturated, substituted and unsubstituted and include among others, alkylene, alkyloxy, alkyne, aryl, haloalkyl, alkylaryl, aryloxy, mercaptoalkyl, aminoalkyl, morpholinoalkyl, sulfoalkyl, phenoxyalky, beta-diketo alkyl, alkyl, cyanoalkyl, cyanoalkoxy, and the like or can be partially or wholly halogen substituted.

In general, the organo group should occupy an average area of no more than about 25 $Å^2$ for proper spacing. A combination of larger and smaller groups may be employed when mixed reagents are used.

The process for the formation of the novel inorganic polymers is a metathesis reaction conducted in the presence of a liquid medium receptive to the tetravalent metal ion at a temperature up to the boiling point of the liquid medium, preferably from ambient to about 150° C. and, more preferably, to about 100° C. at the pressure employed.

While water is the peferred liquid medium, as most of the carboxy and organophosphorus acid compounds are hygroscopic, an organic solvent such as ethanol may be employed, where water interferes with the reaction or where solubility is to be promoted. There need only to be provided a solvent for the organophosphorus acid compound since the tetravalent ion can be dispersed as a solid in the solvent for slow release of the metal ion for reaction with the organophosphorus acid compound. If it has a sufficiently low melting point, the carboxy phosphorus acid compound may serve as a solvent. Typically, the liquid medium is the liquid medium in which the carboxyphosphorus acid compound is formed.

For complete consumption of the tetravalent compound, the amount of acid employed should be sufficient to provide two moles of phosphorous per mole of tetravalent metal. An excess is preferred. Phosphorous acid and/or phosphoric acid, if present, will enter into the reaction and provide an inorganic polymer diluted in respect of the carboxy groups in proportion to the amount of phosphorous or phosphoric acid employed.

Reaction is virtually instantaneous at all temperatures leading to precipitation of layered crystalline and semi-crystalline inorganic polymer solids.

An amorphous phase may appear as a gel similar to silica gel. The gel can be crystallized by extended reflux in the reaction medium, usually from about 5 to 15 hours. The semi-crystalline product is characterized by a rather broad x-ray powder pattern.

The presence of sequestering agents for the metal ion slows down the reaction and also leads to more highly crystalline products. For instance, hydrogen fluoride is a sequestering agent for zirconium and nitrate ion a sequestering agent for thorium. Both slow the reaction and promote the formation of highly crystalline end products.

As compared to zirconium phosphate forming crystals of 1-5 microns, the crystals of 100 to 1000 microns in size have been prepared.

A property critical for many of the likely uses of the products of this invention is thermal stability. This is because deficiencies in activity can be compensated for by reasonable increases in operating temperature. A standard method for thermal characterization is thermal gravimetric/differential thermal analysis (TGA/DTA). These techniques indicate changes in weight and heat flow of substances as a function of temperature. Thus, decomposition and phase changes can be monitored as temperature increases.

Zirconium phosphate itself is quite a stable material. Interlayer water is lost at about 100° C., and a second dehydration involving the phosphates occurs above 400° C. The practical ion-exchanging abilities are lost in this step.

The inorganic polymers of this invention are also stabilized toward thermal decomposition as compared to pure organic analogs as a result of the fixation and separating effect of the inorganic support. Decomposition of zirconium 2-carboxyethyl phosphonate begins between 300° and 400° C. The decomposition process inflection point, approximate midpoint, falls at about 400° C.

Besides proving the suitability of such compounds in elevated temprature applications the TGA analysis affirmed covalent bonding to phosphorus. This is because normal intercalative interactions are reversed within 10°-100° C. above the boiling point of the guest.

The process of preparation permits a wide variety of inorganic polymers to be formed having the characteristic of the organo group protected by the inorganic polymer structure and with subsequent exchange or substitution reactions, the formation of other inorganic polymers. Polymers formed may be block, random and the like.

For instance, a mixture of carboxy phosphorus acid compounds, mixtures of carboxy and organophosphorus acids and organo phosphorus acid compounds may be reacted with one or more of the tetravalent metal ions. If phosphorous and/or phosphoric acid is present, it will enter into the reaction as a reaction diluent.

Another route is to exchange one pendant group for another. The exchange reaction is described in Example 7. While not bound by theory, the present expected points of exchange are at the periphery of the crystal and are schematically illustrated in FIG. 6. Such bifunctional materials exhibit the quality of providing terminal groups for attracting species for intercalation and then interaction with the internal groups.

If a bis acid is present, i.e., when x is 2, interlamellar cross-linking by a reaction such as

will occur where, as in FIG. 6 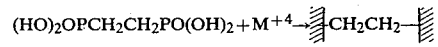 represents the interlamellar layers to which the alkylene group is anchored.

Since size of the linking group will control and fix interlamellar spacing, there is provided effective laminar sieves of fixed spacing for application analogous to that of molecular sieves.

Ion exchange activity was established for the pendant carboxyl groups. Prepared zirconium 2-carboxyethyl phosphonate was established to have an interlayer distance of 12.8 Å. When intercalated to form its n-hexylammonium salt interlayer distance increased to 27.2 Å. When sodium was taken up, layer spacing increased from 12.8 to 14.2 Å. X-ray and infrared data indicated the highly crystalline inorganic polymer to behave as expected for carboxylic acid with behavior analogous to ion exchange resins except that both external and internal surfaces were functional establishing them as super surface ion exchange resins. Moreover, since the inorganic polymers can be prepared as microcrystalline powders, diffusion distances are short.

The high surface area of the crystalline products also make them useful for sorption of impurities from aqueous and non-aqueous media.

Another utility is as an additive to polymeric compositions. Similar to the high aspect ratio provided by solids such as mica which improve the stress strain properties of the polymers, the powdered inorganic polymer products of the invention can serve the same function and add features. By the presence of reactive end groups on the bonded organo groups, chemical grafting to the polymer network can be achieved to increase composite crystallinity and elevating heat distortion temperature. In addition, the presence of phosphorus induces flame retardant properties, as would bound halogen.

Still other utilities include solid lubricants which behave like mica, graphite and molybdenum disulfide; solid slow release agents where intercalated materials can be slowly leached or released from the internal layers of the crystals; substance displaying, electrical, optical phase or field changes with or without doping and the like.

While nowise limiting, the following Examples are illustrative of the preparation of solid inorganic polymers of this invention and some of their utilities.

In the Examples conducted in the atmosphere no extraordinary precautions were taken concerning oxygen or moisture. Reagents were usually used as received from suppliers. The products formed are insoluble in normal solvents and do not sublime. However, the combined weight of yield data, spectroscopy, TGA and powder diffraction results confirm the compositions reported with good reliability.

X-ray powder patterns were run on a Phillips diffractometer using CuK radiation.

Thermal analyses were conducted on a Mettler instrument. Infrared spectra were obtained with a Beckmann Acculab spectrophotometer.

Surface area were determined using both a dynamic flow method, on a Quantasorb instrument, and also with a low temperature static system on a Micromeritic device. Both employ a standard BET interpretation of nitrogen coverage.

Titrations were carried out in aqueous or alcoholic medium. A standard combination electrode and an Orion Ionalyzer pH meter were used for pH determination. The titration of the solid interlamellar anchored materials is analogous to the titration of an ion exchange resin.

EXAMPLE 1

To a 250 ml 3-necked flash fitted with a reflux condenser, stirrer, thermometer and heating mantle, there was charged 21.8 ml of a 38% aqueous solution providing 11.1 g of 2-carboxyethylphosphonic acid in 25 ml of water. Stirring was commenced at room temperature and 9.2 grams of $ZrOCl_2$ in 10 ml of water was added. A white precipitate was immediately formed. Water (17 ml) was added to fluidize the solids and temperature raised to about 90 to about 100° C. to gentle reflux which was continued for 15 hours. The slurry was cooled to room temperature and the white solid isolated by filtration. The solid was washed on the filter with water, acetone, then ether. The solid product was dried to a constant weight of 12.1 grams determined to be semi-crystalline and to have the empirical formula $Zr(O_3PCH_2CH_2COOH)_2$. The x-ray powder diffraction pattern is shown in FIG. 7.

EXAMPLE 2

The procedure of Example 1 repeated except that 4 ml of a 48% aqueous solution of hydrogen fluoride was added to the initial mixture and slowly removed by a slow purge of nitrogen maintained during reflux. The observed to calculated atomic composition was as follows:

| Atom | Observed | Calculated |
|------|----------|------------|
| C    | 18.4%    | 18.23%     |
| H    | 2.84%    | 2.54%      |
| P    | 15.5%    | 15.7%      |

The x-ray diffraction pattern for the highly crystalline product is shown in FIG. 8. Interlayer spacing was determined to be 12.8 Å.

EXAMPLE 3

As in Example 1, there was reacted 1.9 grams of 2-carboxyethylphosphonic acid with 2.3 grams of $Th(NO_3)_4 \cdot 4H_2O$ to yield 1.97 grams of a crystalline solid having the empirical formula $Th(O_3PCH_2CH_2COOH)$ with an interlayer spacing of 14.2 Å.

EXAMPLE 4

As in Example 1, there was reacted 16.1 grams of 2-carboxymethylphosphonic acid with 13.5 grams of $ZrOCl_2 \cdot 8H_2O$ to yield 15.3 grams of a crystalline solid having the empirircal formula $Zr(O_3PCH_2COOH)_2$ with an interlayer spacing of 11.1 Å.

EXAMPLE 5

Diethyl 2-carboethoxyethyl phosphonate was prepared by the Arbuzov reaction of triethyl phosphite and ethyl 3-bromopropionate. The phosphonate ester product was hydrolyzed to the acid in refluxing HBr and then reacted in situ with zirconium ion. The resultant layered compound zirconium 2-carboxyethyl phosphonate, has interlamellar carboxylic acid substituents. The higly crystalline modification had an interlayer distance of 12.8 Å and its n-hexylammonium salt was determined to have interlayer distance of 27.2 Å. Thorium 2-carboxyethyl phosphonate was also prepared in an analogous manner.

The interlamellar carboxylic acid was determined to have a strong carbonyl stretching frequency at 1710 $cm^{-1}$. Upon sodium salt formation this shifts to 1575 and 1465 $cm^{-1}$. The x-ray powder pattern of the sodium salt indicates a layer spacing of 14.2 Å. The x-ray and infrared data of the interlamellar carboxylic acid and its salt indicate that this material behaves as a carboxylic acid. This infrared behavior is analogous to that of ion exchange resins with carboxylic functionality.

The ion exchange behavior of the interlamellar carboxylic acid was investigated in a number of metals. FIG. 10 represents the pH vs. loading profile for the $2H^+—M^{+2}$ exchange of $Cu^{+2}$, $Ni^{+2}$ and $Co^{+2}$ with semicrystalline zirconium 2-carboxyethyl phosphonate. These profiles are in the normal pH range for the exchange of these metals with carboxylic acids.

The influence of crystallinity of the $H^+—Cu^{+2}$ exchange equilibrium is demonstrated in FIG. 10. The pH is about 3.8 for the semi-crystalline and about 4.5 for the high crystalline matrix supporting the anchored functional group influencing the reactivity of the functional group.

The interlamellar metal ion also has an influence on the H+Cu+2 exchange equilibrium. High crystallinity modifications of thorium and zirconium 2-carboxyethylphosphonate were compared. This data is presented in FIG. 11. The thorium compound is the stronger acid by about 0.3 pKa units in this reaction ($pH_{0.5}$=4.2 vs 4.5).

EXAMPLE 6

The reaction rate of zirconium 2-carboxyethylphosphonate with aqueous sodium hydroxide was determined by its addition to an aqueous solution of NaOH with decrease in pH measured as a function of time. As shown in FIG. 12, the concentration of hydroxide ion changed by over three orders of magnitude in 15 seconds representing reaction of 80% of the carboxylic groups. This established that the interlamellar reaction was quite facile and diffusion into the crystal did not involve a high kinetic barrier. Prolonged exposure at a pH of 8 to 10, however, resulted in hydrolysis of the crystal with formation of $ZrO_2$.

EXAMPLE 7

Solid zirconium 2-bromoethyl phosphonate was slurried in an aqueous solution of 2-carboxyethyl phosphonic acid. A trace (1% mol) of HF was added and the mixture refluxed overnight. The infrared spectrum of the solid after this period definitely showed the presence of the carboxylic acid carbonyl band at 1710 $cm^{-1}$. The x-ray powder pattern of the exchanged product was virtually identical to the starting material. This was likely due to the fact that zirconium 2-bromoethyl phosphonate has an interlayer spacing of 13.0 Å and the 2-carboxy analog 12.8 Å. Based on stoichiometry, about 5 to 10% of the sites were exchanged. This being more than the apparent surface site, interlamellar exchange took place.

EXAMPLE 8

Diethyl 3-carboxypropylphosphonate and diethyl 4-carboxybutylphosphonate were prepared by the Arbusov reaction of triethylphosphite and the corresponding bromides. (Method of McConnell & Coover, see Example 5.) These esters were hydrolyzed to the acid and reacted with zirconium ion. The resultant layered compounds zirconium 3-carboxypropyl phosphonate and zirconium 4-carboxybutyl phosphonate had interlayer distances 14.8 Å and 16.4 Å respectively.

EXAMPLE 9

The intermediates in above examples were acquired in the following manner:

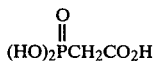

purchased as the triethyl ester from Aldrich Chemical Company.

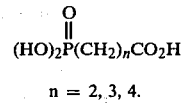

$n = 2, 3, 4.$ prepared by the Arbusov reaction of triethyl phosphite and $Br(CH_2)_nCO_2C_2H_5$, n=2, 3, 4 (purchased from Aldrich Chemical Company) followed by hydrolysis.

What is claimed is:

1. Solid inorganic phosphorus containing polymers providing pendent carboxy groups, and which include structural units of the formula:

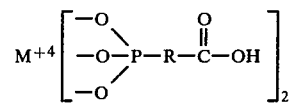

wherein R is an organo group and each oxygen is bonded to phosphorous is structurally linked to a tetravalent metal, M, selected from the group consisting of zirconium, cerium, thorium, uranium, hafnium, lead, titanium and mixtures thereof and wherein the molar ratio of phosphorus to tetravalent metal in said solid inorganic phosphorous containing polyer is about 2 to 1.

2. Solid inorganic phosphorous containing polymers as claimed in claim 1 in which n is 1 and R contains from 1 to about 17 carbon atoms.

3. Solid inorganic phosphorous containing polymers as claimed in claim 1 in which n is 1 and R contains from 1 to about 6 carbon atoms.

4. Solid inorganic phosphonate polymers having the empirical formula:

wherein R is an organo group bonded to phosphorous through carbon and M is a tetravalent metal ion selected from the group consisting of zirconium, cerium, thorium, titanium, uranium, hafnium and lead.

5. Solid inorganic phosphonate polymers as claimed in claim 4 in which R contains from 1 to about 17 carbon atoms.

6. Solid inorganic phosphonate polymers as claimed in claim 4 in which R contains from 1 to about 6 carbon atoms.

7. Inorganic phosphonate polymers having the empirical formula $Zr(O_3PCH_2CH_2COOH)_2$.

8. Inorganic phosphonate polymers having the empirical formula $Zr(O_3PCH_2COOH)_2$.

9. Inorganic phosphonate polymers having the empirical formula $Th(O_3PCH_2CH_2COOH)_2$.

10. Inorganic phosphonate polymers having the empirical formula $Zr(O_3PCH_2CH_2CH_2COOH)_2$.

11. Inorganic phosphonate polymers having the empirical formula $Zr(O_3PCH_2CH_2CH_2COOH)_2$.

* * * * *

UNITED STATES PATENT AND TRADEMARK OFFICE
CERTIFICATE OF CORRECTION

PATENT NO. : 4,235,990
DATED : November 25, 1980
INVENTOR(S) : Peter M. DiGiacomo and Martin B. Dines It is certified that error appears in the above—identified patent and that said Letters Patent is hereby corrected as shown below:

IN THE ABSTRACT:

Next to the last line, change "phosphorous" to -- phosphorus --.

IN THE SPECIFICATION:

Column 1, line 10, change "Organophosphorous" to -- organophosphorus --.
Column 2, line 15, after "composing" insert -- the --.
Column 5, line 1, a new paragraph should begin with the words "FIG. 7".
Column 5, line 37, change "tetravelent" to -- tetravalent --.
Column 5, lines 63 and 64, after "hafnium" insert -- , --.
Column 8, line 17, change "temprature" to -- temperature --.
Column 8, line 31, change "organo phosphorus" to -- organophosphorus --.
Column 8, line 42, change "interclation" to -- intercalation --.
Column 9, line 2, change "make" to -- makes --.
Column 9, line 38, change "Beckmann" to -- Beckman --.
Column 9, line 39, change "were" to -- was --.
Column 10, line 31, change "empirircal" to -- empirical --.
Column 10, line 42, change "higly" to -- highly --.
Column 10, line 53, change "salt" to -- salts --.
Column 12, line 21, change "phosphorous" to -- phosphorus --.
Column 12, line 27, change "phosphorous" to -- phosphorus --.
Column 12, line 27, change "polyer" to -- polymer --.
Column 12, line 29, change "phosphorous" to -- phosphorus --.
Column 12, line 32, change "phosphorous" to -- phosphorus --.
Column 12, line 42, change "phosphorous" to -- phosphorus --.
Column 12, line 46, after "which" insert -- n is 1 and --.

UNITED STATES PATENT AND TRADEMARK OFFICE
CERTIFICATE OF CORRECTION

PATENT NO. : 4,235,990
DATED : November 25, 1980
INVENTOR(S) : Peter M. DiGiacomo and Martin B. Dines It is certified that error appears in the above—identified patent and that said Letters Patent is hereby corrected as shown below:

Page 2

Column 12, line 61, change "$Zr(O_3PCH_2CH_2CH_2COOH)_2$" to -- $Zr(O_3PCH_2CH_2CH_2CH_2COOH)_2$ --.

Signed and Sealed this

Twelfth Day of January 1982

[SEAL]

Attest:

GERALD J. MOSSINGHOFF

Attesting Officer    Commissioner of Patents and Trademarks